United States Patent
Jing Jing et al.

(10) Patent No.: US 11,066,526 B2
(45) Date of Patent: Jul. 20, 2021

(54) METHOD FOR CLEAVING AMIDE BONDS

(71) Applicant: GALDERMA HOLDING S.A., La Tour-de-Peilz (CH)

(72) Inventors: Laura Jing Jing, Antibes (FR); Craig Steven Harris, Biot (FR)

(73) Assignee: Galderma Holding SA, La Tour-de-Peliz (CH)

( * ) Notice: Subject to any disclaimer, the term of this patent is extended or adjusted under 35 U.S.C. 154(b) by 0 days.

(21) Appl. No.: 16/066,967

(22) PCT Filed: Dec. 28, 2016

(86) PCT No.: PCT/EP2016/082770
§ 371 (c)(1),
(2) Date: Jun. 28, 2018

(87) PCT Pub. No.: WO2017/114859
PCT Pub. Date: Jul. 6, 2017

(65) Prior Publication Data
US 2019/0010113 A1   Jan. 10, 2019

(30) Foreign Application Priority Data

| Dec. 29, 2015 | (EP) | 15202944 |
| May 31, 2016 | (EP) | 16172225 |
| May 31, 2016 | (EP) | 16172241 |
| May 31, 2016 | (EP) | 16172254 |

(51) Int. Cl.
| C07C 209/62 | (2006.01) |
| C08J 3/075 | (2006.01) |
| C08B 37/00 | (2006.01) |
| C08B 37/08 | (2006.01) |
| C08L 5/00 | (2006.01) |
| C08J 3/24 | (2006.01) |
| C08L 5/08 | (2006.01) |
| C07C 213/00 | (2006.01) |
| C07C 269/06 | (2006.01) |
| C07F 7/08 | (2006.01) |
| C08J 7/14 | (2006.01) |
| C08K 5/09 | (2006.01) |
| A61K 8/04 | (2006.01) |
| A61K 8/73 | (2006.01) |
| A61Q 19/00 | (2006.01) |
| A61K 9/00 | (2006.01) |

(52) U.S. Cl.
CPC ............ *C08J 3/075* (2013.01); *A61K 8/042* (2013.01); *A61K 8/73* (2013.01); *A61K 8/735* (2013.01); *A61K 9/0019* (2013.01); *A61Q 19/00* (2013.01); *C07C 209/62* (2013.01); *C07C 213/00* (2013.01); *C07C 269/06* (2013.01); *C07F 7/083* (2013.01); *C08B 37/0063* (2013.01); *C08B 37/0069* (2013.01); *C08B 37/0072* (2013.01); *C08J 3/24* (2013.01); *C08J 7/14* (2013.01); *C08K 5/09* (2013.01); *C08L 5/00* (2013.01); *C08L 5/08* (2013.01); *C07C 2603/18* (2017.05); *C08J 2305/00* (2013.01); *C08J 2305/08* (2013.01)

(58) Field of Classification Search
CPC ... C07C 209/62; C07C 213/00; C07C 269/06; C07C 2603/18; C08B 37/0072; C07F 7/083
USPC ........................................................ 536/55.3
See application file for complete search history.

(56) References Cited

U.S. PATENT DOCUMENTS

| 5,332,812 | A | 7/1994 | Nicolson et al. |
| 5,731,298 | A | 3/1998 | Reinmuller |
| 6,132,750 | A | 10/2000 | Perrier et al. |
| 6,495,314 | B1 | 12/2002 | Kent et al. |
| 2004/0072793 | A1* | 4/2004 | Aeschlimann ....... A61K 31/728 514/54 |
| 2004/0219630 | A1* | 11/2004 | Tsubouchi ....... C07K 14/43586 435/68.1 |
| 2006/0166928 | A1 | 7/2006 | Moon et al. |
| 2007/0053987 | A1 | 3/2007 | Bayer et al. |
| 2009/0247741 | A1 | 10/2009 | Zhao |
| 2010/0255068 | A1 | 10/2010 | Stroumpoulis et al. |
| 2013/0203697 | A1 | 8/2013 | Hashimoto et al. |
| 2013/0338352 | A1 | 12/2013 | Yasugi et al. |
| 2014/0094568 | A1 | 4/2014 | James et al. |
| 2015/0045573 | A1 | 2/2015 | Cheng et al. |
| 2019/0016830 | A1 | 1/2019 | Olsson et al. |

FOREIGN PATENT DOCUMENTS

| DE | 44 39 575 A1 | 5/1996 |
| EP | 0 224 987 | 6/1987 |
| EP | 0 903 152 A2 | 3/1999 |
| EP | 1 837 347 A1 | 9/2007 |

(Continued)

OTHER PUBLICATIONS

Crimmins et al. (Current Protocols in Protein Science (2005) 11.4.1-11.4.11).*

(Continued)

*Primary Examiner* — Shaojia A Jiang
*Assistant Examiner* — Michael C Henry
(74) *Attorney, Agent, or Firm* — Foley & Lardner LLP; Sunit Talapatra

(57) ABSTRACT

A method for cleaving amide bonds, comprising:

a) providing a molecule comprising an amide group;

b) reacting the molecule comprising an amide group with hydroxylamine ($NH_2OH$) or a salt thereof to cleave the amide bond of the amide group.

21 Claims, No Drawings

(56) References Cited

FOREIGN PATENT DOCUMENTS

| | | |
|---|---|---|
| EP | 2 609 924 A1 | 7/2013 |
| EP | 2 682 409 | 1/2014 |
| EP | 2 727 597 A1 | 5/2014 |
| EP | 3 020 733 A1 | 5/2016 |
| WO | 97/11958 A1 | 4/1997 |
| WO | 00/01733 A1 | 1/2000 |
| WO | 00/46252 A1 | 8/2000 |
| WO | 00/46253 A1 | 8/2000 |
| WO | 02/18450 A1 | 3/2002 |
| WO | 02/30990 A1 | 4/2002 |
| WO | 02/081739 A2 | 10/2002 |
| WO | 02/082078 A2 | 10/2002 |
| WO | 2015/181365 A1 | 12/2015 |
| WO | 2015/181369 A1 | 12/2015 |

OTHER PUBLICATIONS

Olson et al. (The Journal of Biological Chemistry, vol. 260, No. 6, Issue of Mar. 25, pp. 3784-3790, 1985).*
Babasola et al. (The Journal of Biological Chemistry vol. 289, No. 36, pp. 24779-24791, Sep. 5, 2014).*
International Search Report (PCT/ISA/210) dated Jul. 31, 2017, by the European Patent Office as the International Searching Authority for International Application No. PCT/EP2017/063029.
Written Opinion (PCT/ISA/237) dated Jul. 31, 2017, by the European Patent Office as the International Searching Authority for International Application No. PCT/EP2017/063029.
International Search Report (PCT/ISA/210) dated Feb. 20, 2017, by the European Patent Office as the International Searching Authority for International Application No. PCT/EP2016/082778.
International Search Report (PCT/ISA/210) dated Feb. 20, 2017, by the European Patent Office as the International Searching Authority for International Application No. PCT/EP2016/082781.
International Search Report (PCT/ISA/210) dated Feb. 22, 2017, by the European Patent Office as the International Searching Authority for International Application No. PCT/EP2016/082783.
International Search Report (PCT/ISA/210) dated Feb. 23, 2017, by the European Patent Office as the International Searching Authority for International Application No. PCT/EP2016/082774.
International Search Report (PCT/ISA/210) dated May 10, 2017, by the European Patent Office as the International Searching Authority for International Application No. PCT/EP2016/082770.
Written Opinion (PCT/ISA/237) dated Feb. 20, 2017, by the European Patent Office as the International Searching Authority for International Application No. PCT/EP2016/082778.
Written Opinion (PCT/ISA/237) dated Feb. 20, 2017, by the European Patent Office as the International Searching Authority for International Application No. PCT/EP2016/082781.
Written Opinion (PCT/ISA/237) dated Feb. 22, 2017, by the European Patent Office as the International Searching Authority for International Application No. PCT/EP2016/082783.
Written Opinion (PCT/ISA/237) dated Feb. 23, 2017, by the European Patent Office as the International Searching Authority for International Application No. PCT/EP2016/082774.
Written Opinion (PCT/ISA/237) dated May 10, 2017, by the European Patent Office as the International Searching Authority for International Application No. PCT/EP2016/082770.
Borke, Tina, et al., "Optimized triazine-mediated amidationfor efficient and controlled functionalization of hyaluronic acid", Carbohydrate Polymers 115, pp. 42-50, 2015.
Canova-Davis, Eleanor, et al., "Chemical heterogeneity as a result of hydroxylamine cleavage of a fusion protein of human insulin-like growth factor I", Biochem. J., vol. 285, pp. 207-213, 1992.
D'Este, Matteo, et al., "A systematic analysis of DMTMM vs EDC/NHS for ligation of amines to Hyaluronan in water", Carbohydrate Polymers 108 , pp. 239-246, 2014.
Schanté, Carole E, et al., "Chemical modification of hyaluronic acid for the synthesis of derivatives for a broad range of biomedical applications", Carbohydrate Polymers 85 , pp. 469-489, 2011.
Tomihata, Kenji, et al., "Crosslinking of hyaluronic acid with water-soluble carbodiimide", Research Center for Biomedical Engineering, pp. 243-251, 1995-1996.
Tsigos, Iason, et al., "Chitin deacetylases: new, versatile tools in biotechnology", TIBTECH, vol. 18, pp. 305-312, Jul. 2000.
Zhu, Jeff X., et al., "Selective cleavage of isoaspartyl peptide bonds by hydroxylamine after methyltransferase priming", Analytical Biochemistry 364, pp. 1-7, 2007.
Maleki, Atoosa, et al.; "Characterization of the chemical degradation of hyaluronic acid during chemical gelation in the presence of different cross-linker agents," Carbohydrate Research, vol. 342, (2007), pp. 2776-2792.
Rydergren, Sara, "Chemical Modifications of Hyaluronan using DMTMM-Activated Amidation," Uppsala Universitet, Aug. 2013. (English Abstract only).
Gomes-Rayes et al., "Metal-catalyzed hydroxylaminolysis of unactivated amide and peptide bonds", Org Biomol Chem, vol. 1, 2003 pp. 866-872.
Kurita et al, "Synthetic Carbohydrate Polymers Containing Trehalose Residues in the Main Chain: Preparation and Characteristic Properties", Macromolecules, vol. 27, 1994 pp. 7544-7549.
Diener H.C., "CGRP as a new target in prevention and treatment of migraine", The Lancet: Neurology, 2014 (9 pages).
Hoffman, Organic Chemistry, An Intermediate Text, Second edition, 2004, p. 187 (4 pages).
Lauder R.M., "Chondroitin sulphate: A complex molecule with potential impacts on a wide range of biological systems", Complementary Therapies in Medicine, 2009, vol. 17, pp. 56-62 (7 pages).
Ohshima et al., "Cleavage of unactivated amide bonds by ammonium salt-accelerated hydrazinolysis", ChemComm, 2014, pp. 12623-12625 (4 pages).
Ohshima et al., "Microwave-Assisted Deacylation of Unactivated Amides using Ammonium-Salt-Accelerated Transamidation", Angewandte Communications, 2012, vol. 51, pp. 8564-8567 (4 pages).
Paterson et al., "Carbohydrate-Based Crosslinking Agents: Potential Use in Hydrogels", Journal of Polymer Science Part A: Polymer Chemistry, vol. 49, pp. 4312-4315 (4 pages).
Rapoport, A., "Commentary: The End of the Line for a Novel Migraine Drug?", Neurology Reviews, 2009, 17(10):12 (2 pages).

* cited by examiner

METHOD FOR CLEAVING AMIDE BONDS

TECHNICAL FIELD OF THE INVENTION

The present invention relates to methods for cleaving amide bonds in organic molecules comprising amide groups. Such methods find use in various organic synthetic applications, e.g. for deacetylation.

BACKGROUND OF THE INVENTION

Traditional methods to cleave amide bonds via saponification or hydrolysis are harsh processes requiring strongly basic conditions (i.e. concentrated NaOH or the like) or strongly acidic conditions (i.e. concentrated HCl or the like) at elevated temperatures for long periods of time. Because of the harsh conditions required, these methods have major chemical compatibility issues with regard to protecting groups and to preservation of chiral centers during the reaction.

Among the more recent methods cited is hydrazinolysis. Hydrazine permits the cleavage of amide bonds under almost anhydrous conditions. Hydrazine is a powerful nucleophile thanks to the alpha effect, and its reduced basicity as compared to NaOH permits the cleavage of amide bonds in the presence of other protecting groups and the preservation of certain chiral centres. This was recently highlighted in two high profile publications from Ohshima et al. (Angew. Chem. Int. Ed. 2012, 51, 8564-8567 and Chem. Commun., 2014, 50, 12623-12625). In these two communications Ohshima used ethylene diamine and hydrazine in the presence of ammonium salts, respectively, under microwave irradiation to cleave amide bonds while maintaining other sensitive protecting groups and chiral centers.

Even in the light of the recent findings of Ohshima et al. there is still a need in the field for improved and methods allowing for cleavage of amide bonds while preserving protecting groups and chiral centres.

SUMMARY OF THE INVENTION

It is an object of the present invention to provide a method for cleaving amide bonds which can alleviate at least some of the problems in the prior art.

It is an object of the present invention to provide a method for cleaving amide bonds which allows for cleavage of amide bonds while preserving protecting groups and/or chiral centres.

It is a further object of the present invention to provide a method for cleaving amide bonds which does not require strongly basic conditions (i.e. concentrated NaOH or the like) or strongly acidic conditions (i.e. concentrated HCl or the like) at elevated temperatures for long periods of time.

According to aspects illustrated herein, there is provided a method for cleaving amide bonds, comprising:
a) providing a molecule comprising an amide group;
b) reacting the molecule comprising an amide group with hydroxylamine ($NH_2OH$) or a salt thereof to cleave the amide bond of the amide group.

An "amide group" as referred to herein, is a compound with the functional group $R_nE(O)_xNR'_2$ (wherein R and R' refer to H or organic groups). Most common are carboxamides (organic amides) (n=1, E=C, x=1), but other important types of amides are known, including phosphoramides (n=2, E=P, x=1 and many related formulas) and sulfonamides (E=S, x=2) (IUPAC, Compendium of Chemical Terminology, 2nd ed. (the "Gold Book") (1997)). The term amide refers both to classes of compounds and to the functional group $R_nE(O)_xNR'_2$ within those compounds. The bond between the nitrogen atom and the heteroatom in the amide group is referred to herein as the "amide bond".

Thus, in some embodiments the "amide group" is a carboxamide group, a sulfonamide group or a phosphoramide group. The inventive method has been found to be particularly useful for cleaving amides which are typically more difficult to cleave, such as carboxamides or sulfonamides. Accordingly, in some embodiments the "amide group" is a carboxamide group or a sulfonamide group. In a preferred embodiment, the "amide group" is a carboxamide group. Carboxamides are derived from a carboxylic acid and an amine.

The present invention is based on the inventive realization that hydroxylamine ($NH_2OH$) and salts thereof can advantageously be used for cleavage of amide bonds in molecules comprising amide groups under mild reaction conditions. This allows for cleavage of amide bonds while avoiding undesired degradation of the molecule and preserving protecting groups and/or chiral centres. The reaction is illustrated generally by reaction scheme I.

Reaction Scheme I

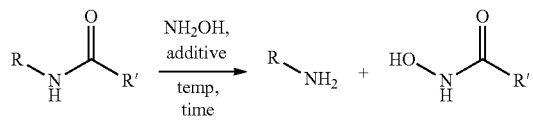

For example, polysaccharides, and particularly glycosaminoglycans such as hyaluronic acid, chondroitin and chondroitin sulfate, are often prone to degradation of the backbone under harsh reaction conditions (e.g. very high or low pH, or high temperatures). The inventive method is therefore especially useful for cleavage of amide bonds in such polysaccharides. The inventive method is for example useful for obtaining at least partially deacetylated glycosaminoglycans in which a significant portion of the molecular weight of the starting material is retained. Using hydroxylamine or salts thereof for deacetylation has been found to allow for N-deacetylation under mild conditions resulting in only minor degradation of the polymeric backbone of hyaluronic acid. Using hydroxylamine or salts thereof for deacetylation thus allows for production of deacetylated hyaluronic acid with retained high molecular weight. This is in contrast to previously known methods, such as deacetylation using hydrazine or NaOH as the deacetylating agent, where high degrees of deacetylation have been inevitably accompanied by severe degradation of the polymeric backbone.

The inventive method is useful for cleaving amide bonds in primary, secondary and tertiary amide groups. A primary amide refers to an amide in which the amide nitrogen is bound to one carbon atom. A secondary amide refers to an amide in which the amide nitrogen is bound to two carbon atoms. A tertiary amide refers to an amide in which the amide nitrogen is bound to three carbon atoms. The method is particularly advantageous for cleaving amide bonds in more hindered amides, i.e. secondary and tertiary amide groups, since such bonds are typically more difficult to cleave using conventional methods. Thus, according to embodiments, the amide group is a primary, secondary or tertiary amide group, preferably a secondary amide group.

The inventive method may also be particularly useful for deacylation, particularly deacetylation, of molecules comprising acyl or acetyl groups. Thus, according to embodiments, the amide group is an N-acyl amide group, preferably an N-acetyl amide group.

According to embodiments, the molecule comprising an amide group further comprises a pH sensitive chiral center. Examples of molecules comprising an amide group and further comprising a pH sensitive chiral center include, but are not limited to, certain oligosaccharides, polysaccharides, and amino acids.

As evidenced by the attached Examples, cleavage of amide bonds in a molecule using hydroxylamine or salts thereof can also be achieved without cleaving common protecting groups present in the molecule.

According to embodiments, the molecule comprising an amide group further comprises a pH sensitive protecting group. By "pH sensitive protecting group", we mean a protecting group which is cleaved off under high or low pH conditions. By high pH in this context we generally mean a pH of 12 or higher conditions (e.g. concentrated NaOH or the like). By low pH in this context we generally mean a pH of 2 or lower (e.g. concentrated HCl or the like). Examples of pH sensitive protecting groups include, but are not limited to Boc (tert-Butyloxycarbonyl), Fmoc (9-Fluorenylmethyl-oxycarbonyl), Cbz (Carbobenzyloxy), i-PrCO, t-BuCO and Tr (triphenylmethyl).

According to some embodiments, the molecule comprising an amide group is a biopolymer comprising acetyl groups. According to some embodiments, the biopolymer comprising acetyl groups is a glycosaminoglycan. According to some embodiments, the biopolymer comprising acetyl groups is selected from the group consisting of sulfated or non-sulfated glycosaminoglycans such as hyaluronan, chondroitin, chondroitin sulphate, heparan sulphate, heparosan, heparin, dermatan sulphate and keratan sulphate, preferably hyaluronic acid, chondroitin and chondroitin sulfate, and mixtures thereof. According to some embodiments, the biopolymer comprising acetyl groups is hyaluronic acid. In some embodiments, the biopolymer is a hyaluronic acid gel. In some embodiments, the biopolymer is a hyaluronic acid gel crosslinked by 1,4-butanediol diglycidyl ether (BDDE).

Hyaluronic acid is one of the most widely used biocompatible polymers for medical use. Hyaluronic acid and the other GAGs are negatively charged heteropolysaccharide chains which have a capacity to absorb large amounts of water. Hyaluronic acid and products derived from hyaluronic acid are widely used in the biomedical and cosmetic fields, for instance during viscosurgery and as a dermal filler.

According to embodiments, a product formed by the cleavage of the amide bond of step b) is an amine.

According to embodiments, the method further comprises the step c) recovering a product, preferably an amine, formed by the reaction of step b).

The recovery in step c) may comprise any suitable organic synthetic work-up or purification technique or combination of techniques.

The reaction temperature in step b) is preferably selected so as not to cause excessive degradation of the molecule and so as to preserve protecting groups and/or chiral centres. The reaction may generally be performed at a temperature of 200° C. or less, such as a temperature of 150° C. or less. According to embodiments, the reaction in step b) comprises reacting the molecule comprising an amide group with the hydroxylamine or salt thereof at a temperature of 100° C. or less. According to embodiments, the reaction in step b) comprises reacting the molecule comprising an amide group with the hydroxylamine or salt thereof at a temperature in the range of 10-100° C., preferably 20-90° C., preferably 30-70° C., preferably 30-50° C. The temperature may for example be in the range of 70-90° C., such as about 80° C., or in the range of 30-50° C., such as about 40° C.

The reaction time in step b) depends on the desired degree of amide cleavage. The reaction time is preferably selected so as not to cause excessive degradation of the molecule and so as to preserve protecting groups and/or chiral centres, and is also dependent on the temperature and pH. The reaction time may generally be anywhere from 5 minutes to 200 hours or more. According to some embodiments, the reaction in step b) comprises reacting the molecule comprising an amide group with the hydroxylamine or salt thereof for 2-200 hours. According to some embodiments, the reaction in step b) comprises reacting the molecule comprising an amide group with the hydroxylamine or salt thereof for 2-150 hours, preferably 5-150 hours, preferably 5-100 hours. In other embodiments, e.g. where a higher temperature or pH is used, the reaction time can be much shorter, such as in the range of 5 minutes to 2 hours, in the range of 30 minutes to 2 hours, or in the range of 1-2 hours. Likewise, under otherwise mild reaction conditions, the reaction time can be much longer than 200 hours.

The cleavage of the amide bond can be achieved using hydroxylamine or salt thereof. The hydroxylamine salt refers to a salt formed by hydroxylamine and an acid. The hydroxylamine salt may for example be a salt formed by hydroxylamine and an acid selected from the group consisting of mineral acids and organic acids or mixtures thereof.

According to embodiments, the hydroxylamine salt is a salt formed by hydroxylamine and a mineral acid. According to embodiments, the acid is selected from the group consisting of sulfuric acid, hydrochloric acid, hydroiodic acid, hydrobromic acid and phosphoric acid, and combinations thereof. Preferred mineral acids include hydrochloric acid, hydroiodic acid and hydrobromic acid. A particularly preferred mineral acid is hydroiodic acid.

According to embodiments, the hydroxylamine salt is a salt formed by hydroxylamine and an organic acid. According to embodiments, the acid is selected from the group consisting of acetic acid, propionic acid, pivalic acid, citric acid, oxalic acid, malonic acid, lactic acid, benzoic acid, and halogenated carboxylic acids, such as trifluoroacetic acid (TFA) and trichloroacetic acid, and combinations thereof.

According to embodiments, the acid is selected from the group consisting of acetic acid, propionic acid, pivalic acid, and a halogenated carboxylic acid, preferably trifluoroacetic acid, and combinations thereof. According to embodiments, the acid is a halogenated carboxylic acid, preferably trifluoroacetic acid.

According to embodiments, the hydroxylamine salt is a salt formed by hydroxylamine and an acid selected from the group consisting of hydrochloric acid, hydroiodic acid and hydrobromic acid, propionic acid, pivalic acid and trifluoroacetic acid.

The reaction in step b is preferably performed in a solvent capable of at least partially dissolving both the molecule comprising an amide group and the hydroxylamine or salt thereof. The solvent may for example be water or an organic solvent or a mixture thereof. Non-limiting examples of preferred solvents include water or a mixture of water and a lower alcohol, such as ethanol. However, may other solvents would be useful, depending on the particular molecule comprising the amide group to be cleaved, and the selection of hydroxylamine or salt thereof. One example of a useful organic solvent is tetrahydrofuran (THF).

According to embodiments, the reaction in step b) comprises reacting the molecule comprising an amide group with hydroxylamine in water.

The method may preferably be performed in water or aqueous solution, optionally further comprising another solvent, such as ethanol. Thus according to some embodiments, step b) comprises contacting a molecule comprising an amide group with hydroxylamine in water so that an aqueous mixture or solution of the molecule and the hydroxylamine is formed.

According to embodiments, the concentration of hydroxylamine in step b) is at least 10% by weight, preferably at least 20% by weight, preferably at least 30% by weight. A higher concentration of hydroxylamine may increase the reaction rate.

Hydroxylamine is often provided in the form of an aqueous solution, typically at a concentration of 50% by weight. In some embodiments, the molecule comprising an amide group may be mixed and dissolved directly in the aqueous solution of hydroxylamine, optionally diluted. Alternatively, a solid salt of hydroxylamine, for example hydroxylamine hydrochloride or hydroxylamine sulfate, can be dissolved in an aqueous solution of the molecule comprising an amide group. Adding a salt of hydroxylamine, and converting the salt to hydroxylamine, may be done as an alternative or as a complement to dissolving the molecule comprising an amide group in an aqueous solution of hydroxylamine.

The molar concentration of hydroxylamine in the reaction mixture is preferably in the range of 5-20 M. For example, a concentration of hydroxylamine of 50% by weight roughly corresponds to a molar concentration of 16 M.

The inventors have surprisingly found that when a hydroxylamine salt is used instead of hydroxylamine itself, the same reaction rate can be achieved with a significantly lower molar concentration. Thus, the molar concentration of hydroxylamine salt in the reaction mixture is preferably in the range of 0.01-10 M, preferably in the range of 0.1-5 M.

According to some embodiments, the molecule comprising an amide group is dissolved in an aqueous solution of hydroxylamine or salt thereof in step a). According to some embodiments, a salt of hydroxylamine is dissolved in an aqueous solution of a molecule comprising an amide group in step a). According to some embodiments, the molecule comprising an amide group is dissolved in an aqueous solution of hydroxylamine, and a salt of hydroxylamine is dissolved in the aqueous solution of the molecule comprising an amide group in hydroxylamine.

The pH in the reaction step b) is preferably selected so as not to cause excessive degradation of the molecule and so as to preserve protecting groups and/or chiral centres. The pH of a 50% v/v solution of hydroxylamine in water is 10.2. According to some embodiments, the reaction in step b) is performed at a pH value in the range of 4-12. According to some embodiments, the reaction in step b) is performed at a pH value in the range of 9-11. According to some embodiments, the reaction in step b) is performed at a pH value in the range of 4-9, preferably in the range of 6-8.

The inventors have found through extensive experimentation that addition of a pH reducing agent can significantly increase the reaction rate of the reaction in step b), particularly when hydroxylamine is used. This effect is both surprising and highly advantageous. It is noted that a corresponding addition of a pH reducing agent to a hydrazine amide cleavage reaction did not result in any increase of the reaction rate. A lower pH value during the reaction is also preferred in order to avoid excessive degradation of the molecule and so as to preserve protecting groups and/or chiral centres.

Thus, according to some embodiments, the pH of the reaction is lowered by addition of a pH reducing agent. According to some embodiments, the pH of the reaction is lowered to a value in the range of 4-9, preferably in the range of 6-8, by addition of a pH reducing agent. The pH reducing agent may for example be selected from the group consisting of mineral acids, organic acids and pH reducing salts, and combinations thereof.

According to embodiments, the pH reducing agent is selected from the group consisting of mineral acids, organic acids and pH reducing salts, and combinations thereof.

According to embodiments, the pH reducing agent is a mineral acid. According to embodiments, the pH reducing agent is selected from the group consisting of sulfuric acid, hydrochloric acid, hydroiodic acid, hydrobromic acid and phosphoric acid, and combinations thereof.

According to embodiments, the pH reducing agent is an organic acid. According to embodiments, the pH reducing agent is selected from the group consisting of acetic acid, propionic acid, pivalic acid, citric acid, oxalic acid, malonic acid, lactic acid, benzoic acid, and halogenated carboxylic acids, such as trifluoroacetic acid and trichloroacetic acid, and combinations thereof. According to embodiments, the pH reducing agent is selected from the group consisting of acetic acid, propionic acid, pivalic acid, and a halogenated carboxylic acid, preferably trifluoroacetic acid, and combinations thereof. According to embodiments, the pH reducing agent is a halogenated carboxylic acid, preferably trifluoroacetic acid.

According to embodiments, the pH reducing agent is a pH reducing salt. According to embodiments, the pH reducing agent is selected from the group consisting of ammonium chloride, ammonium bromide, ammonium iodide, hydroxylamine hydrochloride and hydroxylamine sulfate, and combinations thereof. According to embodiments, the pH reducing agent is selected from the group consisting of hydroxylamine hydrochloride or hydroxylamine sulfate, preferably hydroxylamine hydrochloride.

According to some embodiments, the reaction in step b) is performed in inert atmosphere and/or in darkness.

The present invention is based on the inventive realization that hydroxylamine ($NH_2OH$) and salts thereof can advantageously be used for cleaving an amide bond in a molecule comprising an amide group under mild reaction conditions. Thus according to other aspects illustrated herein, there is provided the use of hydroxylamine or a salt thereof for cleaving an amide bond in a molecule comprising an amide group.

The use may be further characterized as described above with reference to the method.

Other aspects and preferred embodiments of the present invention will be evident from the following Examples and the appended claims.

The term "molecular weight" as used herein in connection with various polymers, e.g. polysaccharides, refers to the weight average molecular weight, $M_w$, of the polymers, which is well defined in the scientific literature. The weight average molecular weight can be determined by, e.g., static light scattering, small angle neutron scattering, X-ray scattering, and sedimentation velocity. The unit of the molecular weight is Da or g/mol.

The person skilled in the art realizes that the present invention by no means is limited to the preferred embodiments described herein. On the contrary, many modifications and variations are possible within the scope of the appended claims. Additionally, variations to the disclosed embodiments can be understood and effected by the skilled person in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

EXAMPLES

Without desiring to be limited thereto, the present invention will in the following be illustrated by way of examples.

Analysis Methods $^1$H NMR spectra were recorded on a BRUKER Biospin AVANCE 400 spectrometer. Chemical shifts are reported as δ values downfield from internal TMS in appropriate organic solutions. The purity and the structures of the products were confirmed by LCMS (254 nm) on a Waters 2690 photodiode array detector system using the following conditions: Column, Symmetry C-18; Solvent A, water 0.1% formic acid; Solvent B, $CH_3CN$; flow rate, 2.5 ml/min; run time, 4.5 min; gradient, from 0 to 100% solvent B; mass detector, micro mass ZMD. Purifications were carried out directly by mass-triggered preparative LCMS Waters X-Terra reverse-phase column (C-18, 5 microns silica, 19 mm diameter, 100 mm length, flow rate of 40 ml/minute) and decreasingly polar mixtures of water (containing 0.1% formic acid) and acetonitrile as eluent. The fractions containing the desired compound were evaporated to dryness to afford the final compounds usually as solids.

Example 1

Preparation of N-((2R,3R,4S)-1,3,4,5-tetrahydroxy-6-(trityloxy)hexan-2-yl)acetamide

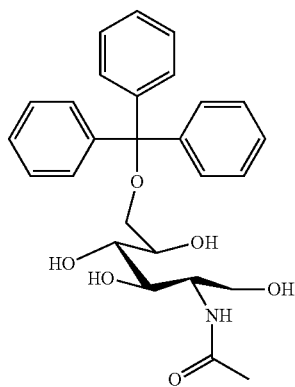

A solution of N-((2R,3S,5S)-2,4,5-trihydroxy-6-trityloxymethyl-tetrahydro-pyran-3-yl)-acetamide (556 mg, 1.20 mol, 1.00 eq.) in a mixture of $THF-H_2O$ (20 ml, 4:1) at r.t., was treated with solid sodium borohydride (49.92 mg, 1.32 mol, 1.10 eq.) [gas evolution]. The reaction mixture was stirred at r.t. for 2 h, concentrated to dryness to afford N-((2R,3R,4S)-1,3,4,5-tetrahydroxy-6-(trityloxy)hexan-2-yl)acetamide (500 mg, 89.54%) as a white solid that was used without further purification.

LCMS: $t_R$=1.01 min., purity=100%; ES+, 464.26 (M–H)$^-$.

Example 2

Deacetylation of N-((2R,3R,4S)-1,3,4,5-tetrahydroxy-6-(trityloxy)hexan-2-yl)acetamide A suspension of N-((2R,3R,4S)-1,3,4,5-tetrahydroxy-6-(trityloxy)hexan-2-yl)acetamide (1 eq) in hydroxylamine (10 volumes) was either treated with acid additives to lower the pH to 7 or not as set out in Table 1, Examples 1-10. The mixture was heated at 80° C. until full conversion of the deacetylation was reached. Deacetylation of N-((2R,3R,4S)-1,3,4,5-tetrahydroxy-6-(trityloxy)hexan-2-yl)acetamide with hydrazine (pH 13) under the same conditions as in Example 2-1 is also included as Example 2-10.

The results are displayed in Table 1. The results show that the deacetylation procedure proceeds considerably faster with hydroxylamine than with hydrazine, and is significantly by the addition of a pH reducing agent.

TABLE 1

| Example | Solvent (50 vols)* | Additive | pH | Time to reach 100% conversion |
|---|---|---|---|---|
| 2-1 | 50% $NH_2OH$ (aq) | None | 10.2 | 72 h |
| 2-2 | 50% $NH_2OH$ (aq) | HCl | 7 | 12 h |
| 2-3 | 50% $NH_2OH$ (aq) | HBr | 7 | 9 h |
| 2-4 | 50% $NH_2OH$ (aq) | HI | 7 | 5 h |
| 2-5 | 50% $NH_2OH$ (aq) | $H_2SO_4$ | 7 | 29 h |
| 2-6 | 50% $NH_2OH$ (aq) | $CH_3COOH$ | 7 | 6 h |
| 2-7 | 50% $NH_2OH$ (aq) | TFA | 7 | 4 h |
| 2-8 | 50% $NH_2OH$ (aq) | $(CH_3)_3COOH$ | 7 | 5 h |
| 2-9 | 50% $NH_2OH$ (aq) | $CH_3CH_2COOH$ | 7 | 8 h |
| 2-10 | $NH_2NH_2 \cdot H_2O$ | None | 13 | 120 h |

The reaction mixtures were purified directly by Preparative LCMS to afford (2R,3R,4S)-2-amino-6-(trityloxy)hexane-1,3,4,5-tetraol as a white solid.

LCMS: $t_R$=0.88 min., purity=99%; ES+, 422.11 (M–H)$^-$.
$^1$H NMR (DMSO-$d_6$) δ: 7.47-7.37 (m, 6H), 7.30 (dd, J=8.3, 6.7 Hz, 6H), 7.26-7.15 (m, 3H), 3.92 (m, 1H), 3.83-3.74 (m, 1H), 3.62-3.53 (m, 1H), 3.52-3.41 (m, 1H), 3.34-3.27 (m, 1H), 3.22-3.16 (m, 1H), 3.13-3.04 (m, 1H), 3.01-2.91 (m, 1H)

Example 3

Preparation of N-(4-aminophenethyl)acetamide

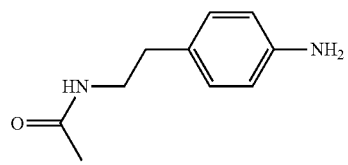

A 4-(2-aminoethyl)aniline (1.50 g; 11.01 mmol; 1.00 eq.) was added neat p-cresyl acetate (1.65 g, 11.0 mmol, 1.00 eq.) and the reaction mixture was stirred at room temperature for 30 h. The resulting orange solution was absorbed directly on silica gel and purified by flash chromatography (silica gel, DCM/MeOH 0-5%) to afford N-(4-aminophenethyl)acetamide (1.76 g, 89.7% yield)

LCMS: $t_R$=0.58 min., purity=99.5%; ES+, 179.5 (M+H)$^+$.

$^1$H-NMR (400 MHz, DMSO-d$_6$) δ 1.78 (s, 3H), 2.50 (m, 2H hidden by DMSO signal) 3.14 (m, 2H), 4.83 (s, 2H), 6.49 (d, J=7.5 Hz, 2H), 6.84 (d, J=7.5 Hz, 2H), 7.82 (s, 1H).

Example 4

Preparation of tert-butyl (4-(2-acetamidoethyl)phenyl)carbamate

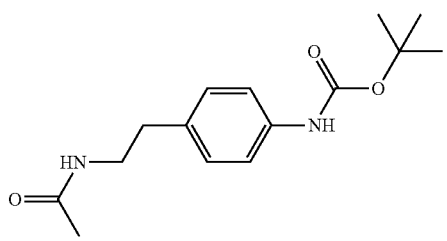 [SMILES: CC(=O)NCCc1ccc(NC(=O)OC(C)(C)C)cc1]

To a stirred solution of N-[2-(4-Amino-phenyl)-ethyl]-acetamide (500 mg, 2.81 mmol, 1.00 eq.) in DCM (20 ml) at r.t., was added triethylamine (0.51 ml, 3.65 mmol, 1.30 eq.) followed by di-tert-butyl dicarbonate (673.48 mg, 3.09 mmol, 1.10 eq.). The reaction mixture is stirred at r.t. for 1 h, washed with water (5 ml), a saturated solution of NaHSO$_4$ (aq) (5 ml) and water (3×5 ml), dried over MgSO$_4$ and concentrated to dryness to afford tert-butyl (4-(2-acetamidoethyl)phenyl)carbamate (496 mg, 63% yield) as a pale orange solid.

LCMS: $t_R$=1.11 min., purity=100%; ES+, 279.5 (M+H).

$^1$H-NMR (DMSO-d$_6$) δ 1H NMR (400 MHz, DMSO-d6) δ 1.57 (s, 9H), 1.87 (s, 3H), 2.75-2.64 (m, 2H), 3.36-3.20 (m, 2H), 7.27-7.07 (m, 2H), 7.45 (d, J=8.3 Hz, 2H), 7.94 (t, J=5.6 Hz, 1H), 9.31 (s, 1H).

Example 5

Preparation of NH$_2$OH.HI

To a stirred solution of 50% NH$_2$OH (aq) (9.28 ml, 0.15 mol, 1.00 eq) at 0° C. was added carefully dropwise 57% HI (aq) over a period of 5 minutes until a pH of 7 was achieved. A dense white crystalline solid formed that was collected by filtration, washed carefully with ice cold water to afford hydroxylamine hydrogen iodide (6.80 g, 28%).

Example 6

Preparation of NH$_2$OH.TFA

To a stirred solution of 50% NH$_2$OH (aq) (9.28 ml, 0.15 mol, 1.00 eq) at 0° C. was added carefully dropwise TFA over a period of 5 minutes until a pH of 7 was achieved. The reaction mixture was concentrated under nitrogen sparging to afford hydroxylamine.trifluoroacetate (11.0 g, 98%) as clear colourless oil.

Example 7

Comparative Studies of NH$_2$OH and Salts Thereof Versus Commonly Used Transamidation Agents Such as NH$_2$NH$_2$.H$_2$O and NaOH

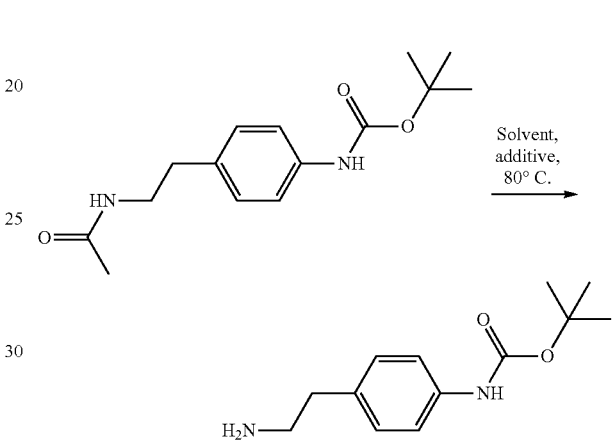

To a stirred solution/suspension of tert-butyl (4-(2-acetamidoethyl)phenyl)carbamate (50 mg, 0.18 mmol) in the chosen solvent (5 volumes) was added the salt (5 eq) and the resulting mixture was heated at 80° C. for the time necessary to complete the reaction. The results are displayed in Table 2. The results show that the deacetylation procedure proceeds quickly with for example hydroxylamine hydrogen iodide (Example 7-3) or hydroxylamine trifluoroacetate (Example 7-9), even when the relative concentration of hydroxylamine in the salts is much lower than the concentration of hydroxylamine alone in Example 7-1.

LCMS: $t_R$=0.81 min., purity=100%; ES+, 237.51 (M+H)$^+$.

$^1$H-NMR (DMSO-d$_6$) δ 1H NMR (400 MHz, DMSO-d$_6$) δ 9.26 (s, 1H), 8.40 (s, 1H), 7.38 (d, J=8.0 Hz, 2H), 7.11 (d, J=8.0 Hz, 2H), 2.89 (m, 2H), 2.80-2.63 (m, 2H), 1.47 (s, 9H) (isolated as formate salt).

TABLE 2

| Example | Solvent (5 vols)* | Additive | pH | 1 h (% conv.) | 2 h (% conv.) | 4 h (% conv.) |
| --- | --- | --- | --- | --- | --- | --- |
| 7-1 | 50% NH$_2$OH (aq) | None | 10.2 | 34.8 | 64.7 | 83.0 |
| 7-2 | 50% NH$_2$OH (aq) | 5 eq NH$_2$OH•HI | 9 | 48.6 | 83.5 | 97.0 |
| 7-3 | EtOH/H$_2$O (4:1) | 5 eq NH$_2$OH•HI | 7 | 63.8 | 85.8 | 98.9 |
| 7-4 | NH$_2$NH$_2$•H$_2$O | None | 13 | 13.6 | 34.9 | 35.2 |
| 7-5 | NH$_2$NH$_2$•H$_2$O | 5 eq NH$_2$OH•HI | 13 | 57.9 | 86.9 | 97.4 |
| 7-6 | EtOH (4 vols) | 4N NaOH (aq) (1 vol) | 14 | 3.7 | 11.63 | 14.5 |

TABLE 2-continued

| Example | Solvent (5 vols)* | Additive | pH | 1 h (% conv.) | 2 h (% conv.) | 4 h (% conv.) |
|---|---|---|---|---|---|---|
| 7-7 | EtOH/H$_2$O (4:1) | 5 eq NH$_2$OH•HCl | 7 | 3.4 | 5.8 | 17.2 |
| 7-8 | EtOH/H$_2$O (4:1) | 5 eq NH$_2$OH•H$_2$SO$_4$ | 7 | 0 | 0.2 | 0.7 |
| 7-9 | EtOH/H$_2$O (4:1) | 5 eq NH$_2$OH•TFA | 7 | 34.2 | 72.4 | 91.3 |
| 7-10 | EtOH/H$_2$O (4:1) | 5 eq NH$_4$I | 7 | 0 | 0 | 0 |

*Volume = 1 g = 1 ml = 1 volume

Example 8

Preparation and Deacetylation of Reduced HA-4 by Hydroxylamine

Diaminotetra-HA (DA-4HA) was synthesized according to the below scheme:

Step 1

A solution of HA-4 (500 mg, 0.61 mmol) in water (5 ml) at room temperature was treated with sodium borohyride (23.05 mg, 0.61 mmol) and the resulting solution was stirred for 3 h, concentrated to dryness to afford the reduced product 1 (532 mg, assumed 100%) as a white foam.

LCMS (t$_r$=0.28 min., ES+=779.4 (M−2Na+2H)

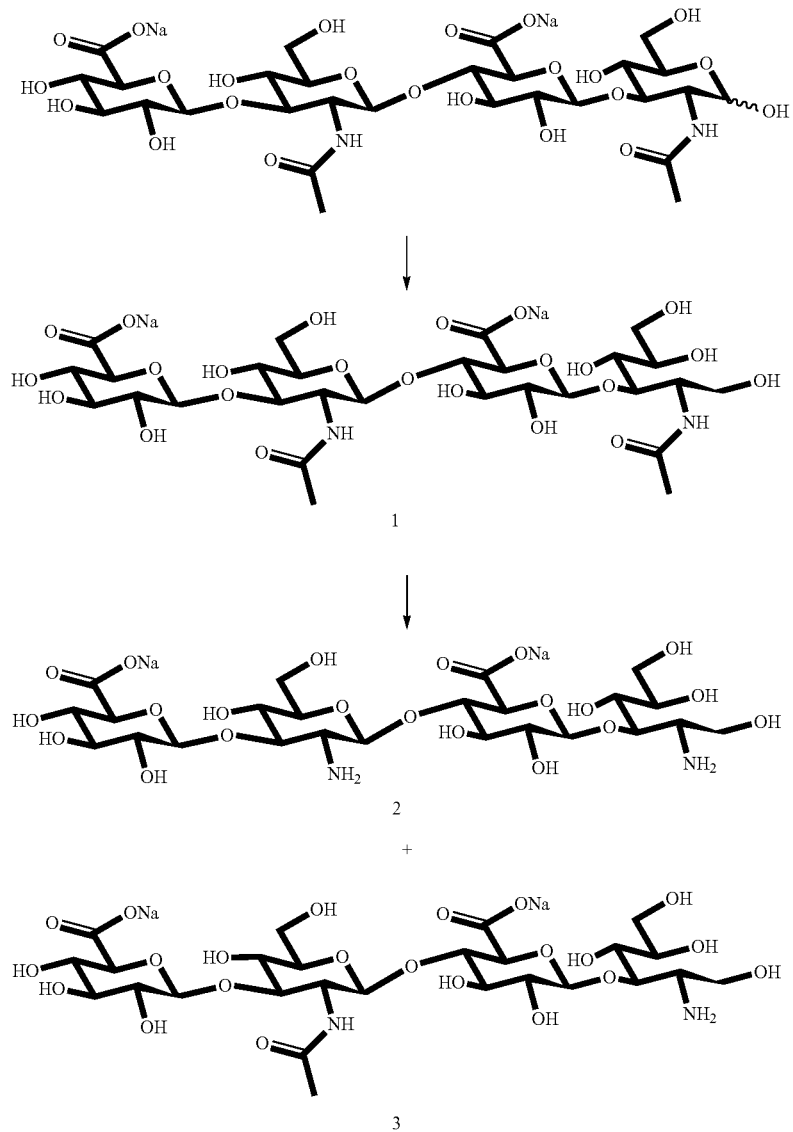

Step 2

The reduced product 1 (532 mg) was dissolved in aqueous NH$_2$OH (5 ml, 50% v/v/) and solid NH$_4$I (100 mg) was added. The resulting suspension was heated at 70° C. for 48 h, cooled to room temperature and concentrated to dryness to afford a residue. The residue was precipitated in neat EtOH and the resulting precipitate was collected by filtration and dried to a constant weight to afford the a 1:1 mixture of diamine 2 and mono-amine 3 in quantitative yield.

2: LCMS (t$_r$=0.16 min., ES+=695.36 (M−2Na+2H)
3: LCMS (t$_r$=0.19 min., ES+=737.47 (M−2Na+2H)

Example 9

Deacetylation of Reduced HA-4 by NH$_2$OH.HI

Reduced HA-4 (532 mg) prepared as described in Step 1 of Example 26, is dissolved in EtOH—H$_2$O (2.5 ml, 1:1) and solid NH$_2$OH.HI (491 mg, 3.05 mmol) is added. The resulting suspension is heated at 80° C. for 6 h, cooled to room temperature and the reaction mixture is purified by Preparative HILIC chromatography to afford deacetylated HA-4 as a white solid. Deacetylated HA-4: LCMS (t$_r$=0.16 min., ES+=695.36 (M−2Na+2H)

Example 10

Deacetylation of Hyaluronic Acid by Hydroxylamine 0.2 g or 20 g of HA (Mw 2 500 kDa, DoA 100%) was solubilised in hydroxylamine (Sigma-Aldrich 50 vol % solution), or a mixture of hydroxylamine/water as set out in Table 3. The solution was incubated in darkness and under argon at 30-70° C. for 5-353 hours. After incubation, the mixture was precipitated by ethanol. The obtained precipitate was filtered, washed with ethanol and then re-dissolved in water. The solution was purified by ultrafiltration and subsequently lyophilized to obtain the deacetylated HA (de-Ac HA) as a white solid. Examples 10-1 to 10-14 were performed using approx. 0.2 g HA and examples 10-15 to 10-16 were performed using 20 g HA. The results are displayed in Table 3. Deacetylation by hydroxylaminolysis is more efficient, and conserves the Mw of the HA backbone better as compared to hydrazinolysis (Example 11) and alkaline methods (Examples 12-13).

TABLE 3

| Example | Temp (° C.) | Time (h) | pH | Conditions | Start Mw (kDa) | NMR DoA (%) | Mw (kDa) |
|---|---|---|---|---|---|---|---|
| 10-1 | 30 | 24 | 10 | NH$_2$OH (50 wt % in water) | 2500 | 99 | 970$^a$ |
| 10-2 | 30 | 72 | 10 | NH$_2$OH (50 wt % in water) | 2500 | 98 | 1060$^a$ |
| 10-3 | 30 | 196 | 10 | NH$_2$OH (50 wt % in water) | 2500 | 95 | 1060$^a$ |
| 10-4 | 40 | 24 | 10 | NH$_2$OH (50 wt % in water) | 2500 | 98 | 1050$^a$ |
| 10-5 | 40 | 72 | 10 | NH$_2$OH (50 wt % in water) | 2500 | 95 | 980$^a$ |
| 10-6 | 40 | 353 | 10 | NH$_2$OH (50 wt % in water) | 2500 | 80 | 490$^a$ |
| 10-7 | 40 | 24 | 10 | NH$_2$OH (35 wt % in water) | 2500 | 99 | 1090$^a$ |
| 10-8 | 40 | 24 | 10 | NH$_2$OH (20 wt % in water) | 2500 | 100 | 1130$^a$ |
| 10-9 | 40 | 24 | 10 | NH$_2$OH (50 wt % in water) | 1000 | 98 | 670$^b$ |
| 10-10 | 55 | 5 | 10 | NH$_2$OH (50 wt % in water) | 2500 | 99 | 1010$^a$ |
| 10-11 | 55 | 72 | 10 | NH$_2$OH (50 wt % in water) | 2500 | 86 | 740$^a$ |
| 10-12 | 55 | 120 | 10 | NH$_2$OH (50 wt % in water) | 2500 | 78 | 400$^b$ |
| 10-13 | 60 | 24 | 10 | NH$_2$OH (50 wt % in water) | 2500 | 92 | 930$^b$ |
| 10-14 | 70 | 24 | 10 | NH$_2$OH (50 wt % in water) | 2500 | 86 | 720$^b$ |
| 10-15 | 40 | 72 | 10 | NH$_2$OH (50 wt % in water) | 2500 | 95 | 1870$^b$ |
| 10-16 | 55 | 72 | 10 | NH$_2$OH (50 wt % in water) | 2500 | 89 | 1050$^b$ |

$^a$SEC-UV
$^b$SEC-MALS

Example 11

Deacetylation of Hyaluronic Acid by Hydrazinolysis—Comparative Example 0.2 g of HA (Mw 2 500 kDa, DoA 100%) was solubilised in 10 mL of a 1% solution of hydrazine sulphate in hydrazine monohydrate. The reaction took place in dark and under argon at 30-55° C. for 24-120 hours. The mixture was precipitated by ethanol. The precipitate obtained was filtered, washed with ethanol and then re-dissolved in water. The final deacetylated HA product was obtained after ultrafiltration, and freeze-dried. The results are displayed in Table 4. Deacetylation by hydrazinolysis gives more degradation of the HA backbone, i.e. lower Mw of the deacetylated product as compared to hydroxylaminolysis (Examples 10-1 to 10-16).

TABLE 4

| Example | Temp (° C.) | Time (h) | pH | Conditions | DoA (%) | Mw (SEC MALS) (kDa) |
|---|---|---|---|---|---|---|
| 11-1 | 30 | 24 | 13 | NH$_2$NH$_2$ + NH$_2$NH$_2$H$_2$SO$_4$ | 100 | 220 |
| 11-2 | 30 | 120 | 13 | NH$_2$NH$_2$ + NH$_2$NH$_2$H$_2$SO$_4$ | 96 | 320 |
| 11-3 | 40 | 48 | 13 | NH$_2$NH$_2$ + NH$_2$NH$_2$H$_2$SO$_4$ | 96 | 260 |
| 11-4 | 40 | 120 | 13 | NH$_2$NH$_2$ + NH$_2$NH$_2$H$_2$SO$_4$ | 92 | 170 |

TABLE 4-continued

| Example | Temp (° C.) | Time (h) | pH | Conditions | DoA (%) | Mw (SEC MALS) (kDa) |
|---|---|---|---|---|---|---|
| 11-5 | 55 | 24 | 13 | $NH_2NH_2$ + $NH_2NH_2H_2SO_4$ | 93 | 60 |
| 11-6 | 55 | 48 | 13 | $NH_2NH_2$ + $NH_2NH_2H_2SO_4$ | 89 | 70 |
| 11-7 | 55 | 72 | 13 | $NH_2NH_2$ + $NH_2NH_2 H_2SO_4$ | 83 | 40 |
| 11-8 | 55 | 120 | 13 | $NH_2NH_2$ + $NH_2NH_2H_2SO_4$ | 77 | 50 |

Example 12

Deacetylation of Hyaluronic Acid by Homogeneous Alkaline Hydrolysis—Comparative Example HA (1 000 kDa) was weighed to a reaction vessel, NaOH solution was added and the reaction was mixed until a homogenous solution was obtained. The mixture was incubated without stirring and subsequently diluted with water and EtOH. The mixture was neutralized by adding 1.2 M HCl, precipitated by adding EtOH. The precipitate was washed with ethanol (70 w/w %) followed by ethanol and dried in vacuum over night to obtain a solid. The results are displayed in Table 5.

Deacetylation by homogenous alkaline hydrolysis gives more degradation of the HA backbone, i.e. lower Mw of the deacetylated product as compared to hydroxylaminolysis (Examples 10-1 to 10-16).

TABLE 5

| Example | Temp (° C.) | Time (h) | pH | Conditions | DoA (%) | Mw (SEC UV) (kDa) |
|---|---|---|---|---|---|---|
| 12 | 65 | 4 | 13 | 1M NaOH (aq.) | 99 | 10 |

Example 13

Deacetylation of Hyaluronic Acid by Heterogeneous Alkaline Hydrolysis—Comparative Example HA (1 000 kDa) was weighed to a reaction vessel and NaOH in EtOH (70% w/w %) was added. The heterogeneous mixture was incubated and subsequently neutralized by addition of 1.2 M HCl. The precipitate was washed with ethanol (75 w/w %) followed by ethanol and dried in vacuum over night to obtain a solid. The results are displayed in Table 6.

Deacetylation by heterogeneous alkaline hydrolysis gives more degradation of the HA backbone, i.e. lower Mw of the deacetylated product as compared to hydroxylaminolysis (Examples 10-1 to 10-16).

TABLE 6

| Example | Temp (° C.) | Time (h) | Conditions | DoA (%) | Mw (SEC UV) (kDa) |
|---|---|---|---|---|---|
| 13 | 35 | 24 | 1.0M NaOH (70% EtOH) | 99 | 60 |

Example 14

Preparation and Deacetylation of benzyl(4-(2-acetamidoethyl)phenyl)-carbamate

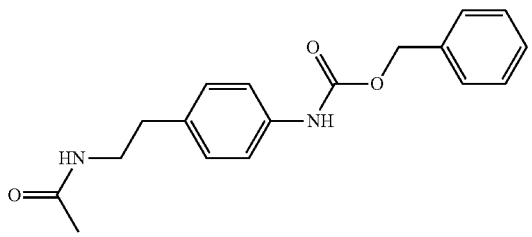 [SMILES: CC(=O)NCCc1ccc(NC(=O)OCc2ccccc2)cc1]

To a stirred solution of N-(4-aminophenethyl)acetamide (200 mg, 1.12 mmol, 1 eq) and TEA (in DCM (10 ml) at 0° C., is added benzyl chloroformate (173 mg, 1.01 mmol) over a period of 5 minutes. The reaction mixture is stirred at room temperature overnight, diluted with DCM 10 ml), washed with a saturated aqueous solution of $NaHSO_4$ (5 ml), water (3×5 ml), dried over $MgSO_4$ and concentrated to dryness to afford the title compound as a white solid.

To a stirred solution of the benzyl (4-(2-acetamidoethyl) phenyl)carbamate (1 eq) in EtOH—$H_2O$ (4:1, 5 volumes) is added $NH_2OH.HI$ (5 eq) and the suspension is heated at 80° C. for 5 h, cooled to room temperature and purified by Mass Triggered Preparative LCMS.

Example 15

Preparation and Deacetylation of allyl(4-(2-acetamidoethyl)phenyl)-carbamate

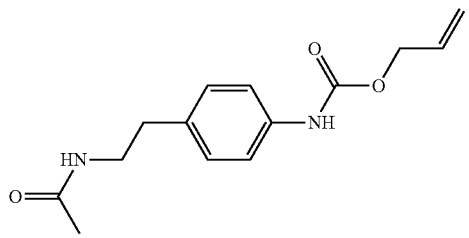 [SMILES: C=CCOC(=O)Nc1ccc(CCNC(C)=O)cc1]

To a stirred solution of N-(4-aminophenethyl)acetamide (200 mg, 1.12 mmol, 1 eq) and TEA (in DCM (10 ml) at 0° C., is added allyl chloroformate (122 mg, 1.01 mmol) over a period of 5 minutes. The reaction mixture is stirred at room temperature overnight, diluted with DCM 10 ml), washed with a saturated aqueous solution of $NaHSO_4$ (5 ml), water (3×5 ml), dried over $MgSO_4$ and concentrated to dryness to afford the title compound as a white solid.

To a stirred solution of the allyl (4-(2-acetamidoethyl) phenyl)carbamate (1 eq) in EtOH—$H_2O$ (4:1, 5 volumes) is

Example 16

Preparation and Deacetylation of (9H-fluoren-9-yl)methyl(4-(2-acetamidoethyl)phenyl)carbamate

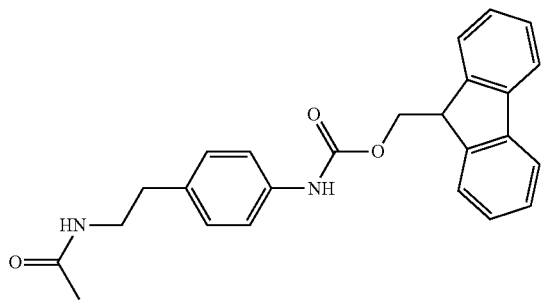 [SMILES: CC(=O)NCCc1ccc(NC(=O)OCC2c3ccccc3-c3ccccc32)cc1]

To a stirred solution of N-(4-aminophenethyl)acetamide (200 mg, 1.12 mmol, 1 eq) and TEA (in DCM (10 ml) at 0° C., is added 9-fluorenylmethyl chloroformate (261 mg, 1.01 mmol) over a period of 5 minutes. The reaction mixture is stirred at room temperature overnight, diluted with DCM 10 ml), washed with a saturated aqueous solution of NaHSO$_4$ (5 ml), water (3×5 ml), dried over MgSO$_4$ and concentrated to dryness to afford the title compound as a white solid.

To a stirred solution of the (9H-fluoren-9-yl)methyl (4-(2-acetamidoethyl)phenyl)-carbamate (1 eq) in EtOH—H$_2$O (4:1, 5 volumes) is added NH$_2$OH.HI (5 eq) and the suspension is heated at 80° C. for 5 h, cooled to room temperature and purified by Mass Triggered Preparative LCMS.

Example 17

Preparation and Deacetylation of 2-(trimethylsilyl)ethyl (4-(2-acetamidoethyl)phenyl)carbamate

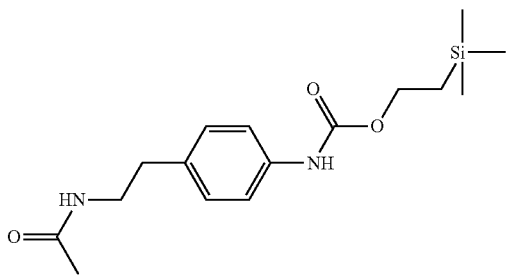 [SMILES: CC(=O)NCCc1ccc(NC(=O)OCC[Si](C)(C)C)cc1]

To a stirred solution of N-(4-aminophenethyl)acetamide (200 mg, 1.12 mmol, 1 eq) and TEA (in DCM (10 ml) at 0° C., is added 4-nitrophenyl 2-(trimethylsilyl)ethyl carbonate (286 mg, 1.01 mmol) over a period of 5 minutes. The reaction mixture is stirred at room temperature overnight, diluted with DCM (10 ml), washed with a saturated aqueous solution of NaHSO$_4$ (5 ml), a saturated solution of NaHCO$_3$ (aq) (5 ml), water (3×5 ml), dried over MgSO$_4$ and concentrated to dryness to afford the title compound as a white solid.

To a stirred solution of the 2-(trimethylsilyl)ethyl (4-(2-acetamidoethyl)phenyl)-carbamate (1 eq) in EtOH—H$_2$O (4:1, 5 volumes) is added NH$_2$OH.HI (5 eq) and the suspension is heated at 80° C. for 5 h, cooled to room temperature and purified by Mass Triggered Preparative LCMS.

The invention claimed is:

1. A method for cleaving amide bonds in glycosaminoglycans, the method comprising reacting a glycosaminoglycan (GAG) comprising an N-acyl amide group with hydroxylamine (NH$_2$OH) or a salt thereof to cleave the amide bond of the amide group.

2. The method according to claim 1, further comprising recovering a product formed by the reaction.

3. The method according to claim 1, wherein the GAG comprises a pH sensitive chiral center.

4. The method according to claim 1, wherein the GAG comprises a pH sensitive protecting group.

5. The method according to claim 1, wherein the reacting is at a temperature of 100° C. or less.

6. The method according to claim 1, wherein the reacting is for 2-200 hours.

7. The method according to claim 1, wherein the reacting is in water.

8. The method according to claim 1, wherein having a molar concentration of hydroxylamine in the range of 5-20 M.

9. The method according to claim 1, wherein the GAG is reacted with a hydroxylamine salt.

10. The method according to claim 9, wherein the hydroxylamine salt is a salt of hydroxylamine and hydroiodic acid or trifluoroacetic acid.

11. The method according to claim 9, having a concentration of the hydroxylamine salt in the range of 0.1-5 M.

12. The method according to claim 9, wherein the reaction is performed in a solvent capable of at least partially dissolving the hydroxylamine salt.

13. The method according to claim 1, wherein the reaction is performed at a pH value in the range of 4-12.

14. The method according to claim 13, wherein the reaction is performed at a pH value in the range of 9-11.

15. The method according to claim 13, further comprising lowering the pH of the reaction to a value in the range of 4-9 by adding a pH reducing agent selected from the group consisting of mineral acids, organic acids and pH reducing salts, and combinations thereof.

16. The method according to claim 15, wherein the pH reducing agent is a pH reducing salt.

17. The method according to claim 1, wherein the GAG is selected from hyaluronic acid, hyaluronan, chondroitin, chondroitin sulphate, heparin sulphate, heparosan, heparin, dermatan sulphate, keratin sulphate, and combinations thereof.

18. The method according to claim 17, wherein the GAG is hyaluronic acid.

19. The method according to claim 1, wherein the GAG is crosslinked in a hydrogel.

20. The method according to claim 1, having a concentration of the hydroxylamine salt in the range of 0.1-10 M.

21. The method according to claim 1, further comprising recovering a product of the reacted GAGs exhibiting a weight average molecular weight of at least about 1,000 kDa.

* * * * *